(12) United States Patent
Lacraz

(10) Patent No.: US 9,724,212 B2
(45) Date of Patent: Aug. 8, 2017

(54) IMPLANT FOR LOWER LIMB AMPUTATION

(71) Applicant: LES HOSPITAUX UNIVERSITAIRES DE GENEVE, Geneva (CH)

(72) Inventor: Alain Lacraz, Cranves-Sales (FR)

(73) Assignee: LES HOPITAUX UNIVERSITAIRES DE GENEVE, Geneva (CH)

( * ) Notice: Subject to any disclaimer, the term of this patent is extended or adjusted under 35 U.S.C. 154(b) by 0 days.

(21) Appl. No.: 14/764,020

(22) PCT Filed: Jan. 28, 2014

(86) PCT No.: PCT/IB2014/058608
§ 371 (c)(1),
(2) Date: Jul. 28, 2015

(87) PCT Pub. No.: WO2014/118701
PCT Pub. Date: Aug. 7, 2014

(65) Prior Publication Data
US 2015/0351940 A1 Dec. 10, 2015

(30) Foreign Application Priority Data
Jan. 29, 2013 (EP) ..................................... 13153017

(51) Int. Cl.
*A61F 2/28* (2006.01)
*A61F 2/78* (2006.01)

(52) U.S. Cl.
CPC .............. *A61F 2/78* (2013.01); *A61F 2/2814* (2013.01); *A61F 2002/2825* (2013.01); *A61F 2002/2892* (2013.01); *A61F 2002/7887* (2013.01)

(58) Field of Classification Search
CPC .. A61F 2/2814; A61F 2/60; A61F 2002/7887; A61F 2002/30884
See application file for complete search history.

(56) References Cited

U.S. PATENT DOCUMENTS 5,593,446 A * 1/1997 Kuoni ................... A61F 2/3676
606/62
5,906,644 A * 5/1999 Powell .................. A61F 2/3609
623/20.15

(Continued)

FOREIGN PATENT DOCUMENTS

DE 3125268 A1 * 1/1983 ............. A61B 17/68
DE 4338746 A1 * 5/1995 ........... A61F 2/2814
DE 19932388 C1 12/2000

OTHER PUBLICATIONS

International Search Report and Written Opinion dated Jan. 28, 2014 issued in PCT Patent Application No. PCT/IB2014/058608.

*Primary Examiner* — Brian Dukert
(74) *Attorney, Agent, or Firm* — Harness, Dickey & Pierce, P.L.C.

(57) ABSTRACT

Implant for transfemoral or transtibial amputation comprising a stem (3) and a base (2), the base (2) comprising a bone support surface (4) on one side and on an opposite side a soft tissue load bearing surface (5). The stem extends from the base perpendicular to the bone support surface and is configured for insertion in a medullary canal (23) of an amputated bone (20), the bone support surface (4) being configured for abutment against a severed end (22) of said amputated bone. A diameter (d1) of the base is configured to be larger than an average diameter of a shaft (21) of said severed bone, the soft tissue load bearing surface (5) comprising a generally planar or slightly curved central portion (10) and a convexly curved radially outward portion (11) with a curvature greater than the central portion, the central (Continued)

portion (10) being oriented at an angle of between 4° to 8° to the bone support surface.

17 Claims, 4 Drawing Sheets

(56) References Cited

U.S. PATENT DOCUMENTS

| | | | | |
|---|---|---|---|---|
| 6,626,913 | B1* | 9/2003 | McKinnon | A61F 2/367 606/86 R |
| 6,709,466 | B1* | 3/2004 | Grundei | A61F 2/2814 623/32 |
| 2007/0150070 | A1 | 6/2007 | Kim et al. | |
| 2010/0016992 | A1* | 1/2010 | Malawer | A61F 2/2814 623/33 |
| 2011/0218639 | A1* | 9/2011 | Shea | A61F 2/30721 623/22.26 |

* cited by examiner

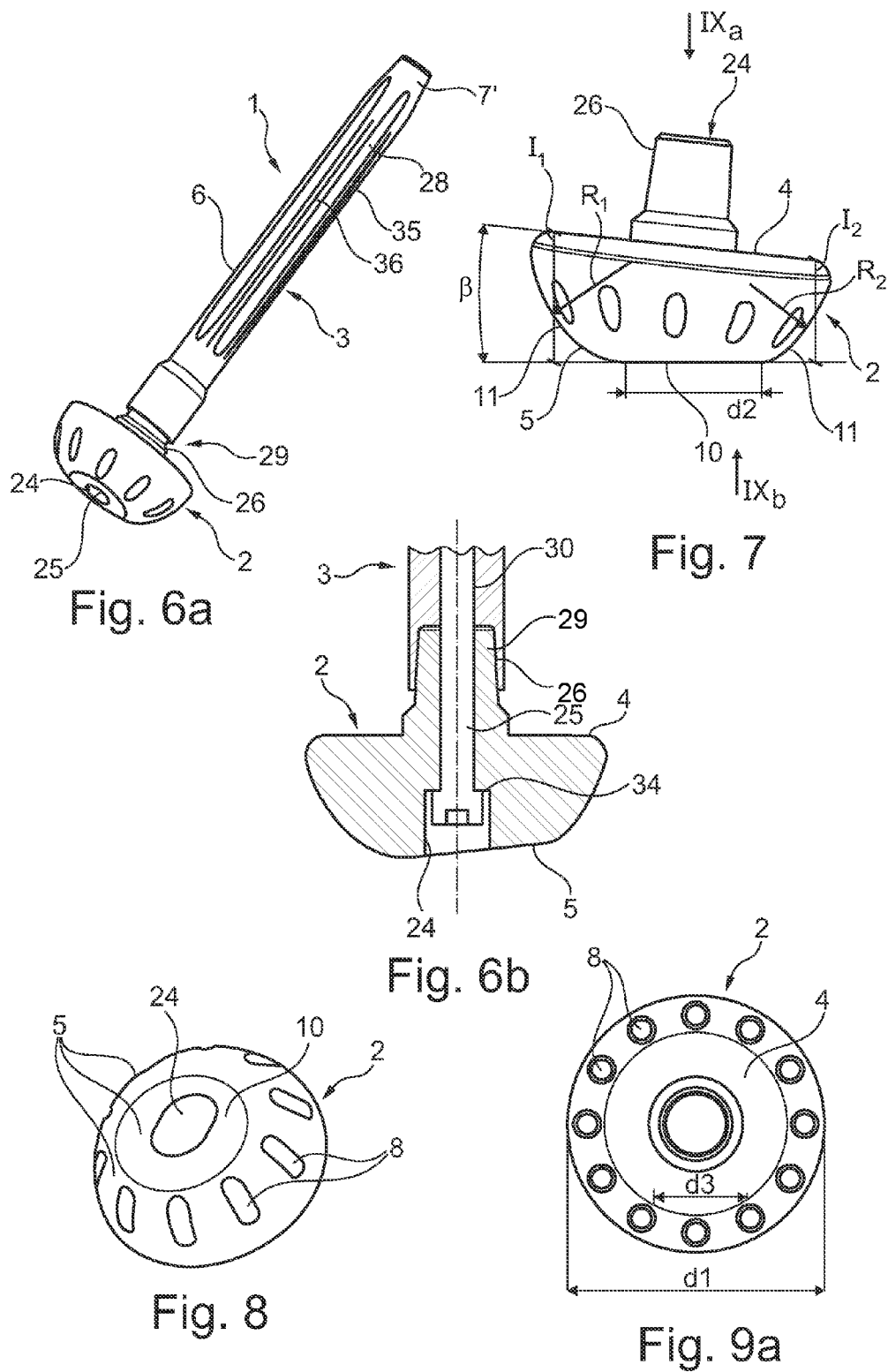

IMPLANT FOR LOWER LIMB AMPUTATION

PRIORITY STATEMENT

This application is a national stage application under 35 U.S.C. §371 of PCT International Application No. PCT/IB2014/058608, which has an International filing date of 28 Jan. 2014 and which claims priority under 35 U.S.C. §119 to European Application No. 13153017.2 filed 29 Jan. 2013. The contents of each application recited above are incorporated herein by reference in their entirety.

FIELD OF THE INVENTION

This invention relates to an implant for distal load bearing in amputation of the lower limb, in particular for above knee amputation.

BACKGROUND OF THE INVENTION

Amputation of the lower limb is one of the most widely performed surgeries. The levels of amputation which decrease the length of the lower limb may generally be divided into two groups: those for which the bone surface after amputation is large enough to accept the distal delivery and those which require a deferred charge area. For above knee amputation, the weight bearing area is on the ischiatic apophysis. Conventional Gritti-Stokes amputation, which is an alternative to long femoral amputation, provides a terminal support. If femoral amputation is more proximal, the Gritti-Stokes amputation technique cannot be performed.

Two amputation levels can thus be distinguished: (i) those for which the distal end of the bony segment, after amputation, provides an area large enough to receive the weight of the patient, and (ii) those for which the severed bone does not provide an area large enough to receive the weight of the patient. The orthopedist technician (prosthetics and orthotics) should thus search for a different support, for instance situated on the ischiatic apophysis in the case of an above knee amputation. For the latter situation, there would be an advantage in providing a distal weight bearing area, avoiding a deferred charge on the ischiatic apophysis and freeing the gluteal zone.

When possible, a Gritti-Stokes amputation offers an interesting alternative in an above knee amputation, consisting in the fixation of the patella by mean of stitches, screws or K-wires. The patella is placed horizontal at the distal end of the femur bone stump. After consolidation, the patella's area supports the distal load. The hard socket goes up to the proximal aspect of the stump, without reaching the ischium. Traditionally this surgery has been indicated in amputations situated in the metaphysal area of the stump (just above the condyles). More proximal, the use of the patella is not recommended since i) its healing (fusion) to the femur is less predictable; and ii) it generates a bulky stump made of infolded muscles (quadriceps) still attached to the patella.

When Gritti-Stokes amputation cannot be implemented, a standard transfemoral amputation is performed; however the distal bony area is too small to receive and allow for end bearing. As a consequence, the patient must either rely on prosthesis with an ischiatic apophysis load, or an implant in the intramedullary canal. This will allow a prosthesis skeleton to be fixed directly on the implant. The latter technique allows the stump's distal load to rest on the prosthesis's skeleton, however, an important drawback is the risk of infection because of the implant passing through the skin. Another risk is the rupture of the intramedullar implant.

SUMMARY OF THE INVENTION

An object of this invention is to provide an implant for lower limb amputation, namely transfemoral or transtibial amputation, to improve the load bearing capacity of the amputation stump.

It is advantageous to provide an implant for transfemoral or transtibial amputation that may be implanted with simple surgical intervention steps.

It is advantageous to provide an implant for transfemoral or transtibial amputation that is versatile and flexible.

It is advantageous to provide an implant for transfemoral or transtibial amputation that improves post operative healing.

It is advantageous to provide an implant for transfemoral or transtibial amputation that improves post operative walking capacity.

It is advantageous to provide a more comfortable prosthesis when walking and sitting, enabling a more efficient gait with lower energy expenditure.

It is advantageous to provide an implant for transfemoral or transtibial amputation that is cost effective.

Objects of this invention have been achieved by providing an implant for transfemoral or transtibial amputation according to claim 1.

Dependent claims describe various advantageous features of the invention.

Disclosed herein is an implant for transfemoral or transtibial amputation comprising a stem and a base, the base having a bone support surface on one side and on an opposite side a soft tissue load bearing surface with a generally rounded profile, the stem extending from the base and being configured for insertion in a medullary canal of a severed bone, and the bone support surface being configured for abutment against a severed end of said amputated bone, a diameter of the base being configured to be larger than an average diameter of a shaft of said severed bone.

In a first aspect of the invention, the bone support surface is oriented perpendicular to the stem and the soft tissue load bearing surface comprises a generally planar or slightly curved central portion and a radially outward portion with a curvature greater than the central portion, the central portion being oriented at an angle of between 4° to 8° to the bone support surface, preferably between 5° to 7°. This advantageously allows the surgical intervention to be simpler, more reliable and accurate while providing an implant that is optimally configured for the anatomical disposition of a patient.

The diameter of the base may be tapered such that proximate the central portion the diameter is less than the diameter of the base proximate the bone support surface.

The base and/or the stem may advantageously be made of a rigid material. The base may be formed of a single piece, which may be integrated with or be separable from the stem.

The central portion and the bone support surface may be substantially circular or oval shaped. The centre of the circular or oval shape of the central portion may be offset from the centre of the circular or oval shape of the bone support surface in a direction towards the convergence of the bone support surface and the angled the central portion surface.

The curved radially outer portion is preferably convexly curved and may be curved such that the radii of curvature is greater distal the direction towards the convergence of the bone support surface and the angled the central portion surface.

The curved radially outer portion of the soft tissue load bearing surface may advantageously have an average radius in the range of 17 mm to 30 mm.

In a second aspect of the invention, the base and stem are separate parts assembled together. This advantageously allows a standard stem or a stem selected from a group consisting of various shaped and/or dimensioned stems to be combined with a standard base or a base selected from a group consisting of various shaped and/or dimensioned bases for optimal configuration taking into account the morphology of a patient.

The stem may advantageously be fixed to the base via a mechanical fixing mechanism comprising a threaded bolt and a complementary threaded bore, the base comprising a passage extending from the bone support surface through the base to receive the bolt therethrough.

In an advantageous embodiment, the base may further comprise a collar portion extending from the bone support surface, through which the passage extends, the collar portion having a conical surface configured to engage a complementary conical surface of the stem for centering and tightly engaging the stem to the base.

In a third aspect of the invention the base advantageously comprise suture holes distributed therearound and extending from the soft tissue load bearing surface to the bone support surface. More particularly, the suture holes may extend from the radially outward portion of the soft tissue load bearing surface. In this way they are easy to access by a medical practitioner during a surgical operation to attach the implant. In an advantageous variant the suture holes are inclined at an angle α such that axes of the suture holes converge on a side opposite the stem, the angle α being a range of 5 to 30°. There may be between 4 and 16 suture holes, preferably 6 to 10 suture holes, distributed evenly around a radially outer surface portion of the base for attaching soft tissue to the implant.

The stem and the base may be made of bio-compatible material selected from a group consisting of stainless steel, titanium, or chrome cobalt alloys.

The soft tissue load bearing surface of the base may comprise a load bearing surface with a generally planar or slightly curved central portion and a radially outward portion with a curvature greater than the central portion. The soft tissue load bearing surface and the bone support surface join together via a rounded corner preferably having a radius of at least 2 mm.

The stem may comprise a straight stem portion and a tapered tip. The stem portion may advantageously have a length in the range of 80 mm to 120 mm.

The implant may further comprise a disposable removable film or cap mounted over the load bearing surface and an outer radial portion of the bone support surface, the removable film or cap configured to cover the suture holes.

In a fourth aspect of the invention the stem comprises a plurality of longitudinal recesses and longitudinal ridges interposed between the recesses and distributed around the stem and extending in an axial direction corresponding to the direction of the medullary canal. The longitudinal ridges may further comprise longitudinal grooves that are narrower than the longitudinal recesses. The longitudinal recesses and grooves allow material or air in the medullary canal to be evacuated suring insertion of the implant, while also allowing bone cement and/or any other osseo-integration promoting material to be received therein to improve anchoring of the stem to the bone.

In a fifth aspect of the invention the implant comprises a polarizing element configured to be engaged by an insertion tool to rotate and position the implant in the correct orientation. Preferably, the polarizing element is arranged on the base, however a polarizing element may additionally or alternatively be arranged on the stem, for example in the case of a separable base and stem. The polarizing element may advantageously be in the form of a slot or other shape adapted for torque transfer.

The above aspects of the invention may be combined in any suitable combination.

Further objects and advantageous aspects of the invention will be apparent from the claims, and from the following detailed description and accompanying figures.

BRIEF DESCRIPTION OF THE FIGURES

FIG. 6a is a view in perspective of an implant for transfemoral or transtibial amputation according to another embodiment of an invention;

FIG. 6b is a cross-sectional view of the base portion and a portion of the stem of the embodiment of FIG. 6a;

FIG. 7 is a side view of a base of the implant illustrated in FIG. 6a;

FIG. 8 is a view in perspective of the base illustrated in FIG. 7;

FIG. 9a is a view in the direction of arrow IXa of FIG. 7;

DETAILED DESCRIPTION OF THE INVENTION

Figure 1:
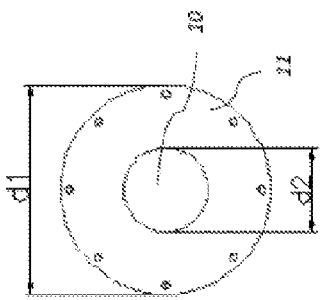
FIG. 1 is a view in perspective of an implant for transfemoral or transtibial amputation according to an embodiment of this invention.

Referring to the figures, an implant 1 for transfemoral or transtibial amputation is shown, comprising a base 2 and a stem 3 configured to be inserted in a medullary canal 23 of an amputated femur bone, and in a variant, in the medullary canal of an amputated tibia bone. The use of the implant according to this invention is most advantageous for transfemoral amputations, however the advantages it confers are also useful for transtibial amputations. For simplicity, the invention embodiments will be described in relation to the amputation of the femur bone, being understood that the invention may also be used in the case of a transtibial amputation with the same features except for dimensional and angular adjustments taking into account the different anatomy of the above knee and below knee parts and bones of a person's leg.

The stem 3 is rigidly connected to, and extends from, the base 2. The stem is manufactured as a separate part configured to be assembled to the base and rigidly attached for example by means of a screw thread connection, or by means of a fixing mechanism 29, as shown in FIGS. 6 to 11. The base and stem are preferably made of a bio-compatible material such as stainless steel or titanium or Chrome Cobalt alloy known per se and widely used in implants such as hip replacement implants subject to high body loads and compatible for in bone mounting, particularly in the bone medullary canal. The stem 3 and the base 2 do not need to be made of the same bio-compatible material. Since the stem 3 should provide good osseo-integration and since the base should provide a good interaction with other human tissue, it may be advantageous to use different bio-compatible materials for the stem 3 and the base 2.

Figure 2:
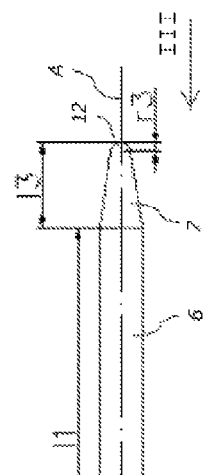
FIG. 2 is a side view of the embodiment of FIG. 1.
Figure 3:
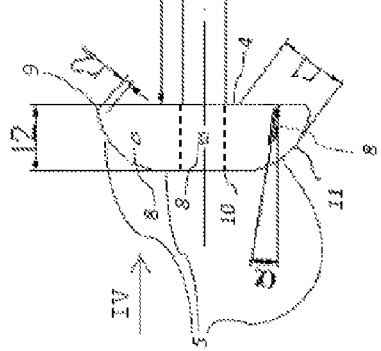
FIG. 3 is a view in the direction of arrow III of FIG. 2.
Figure 4:
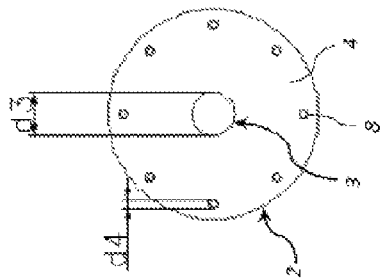
FIG. 4 is a view in the direction of arrow IV of FIG. 2.
Figure 5:
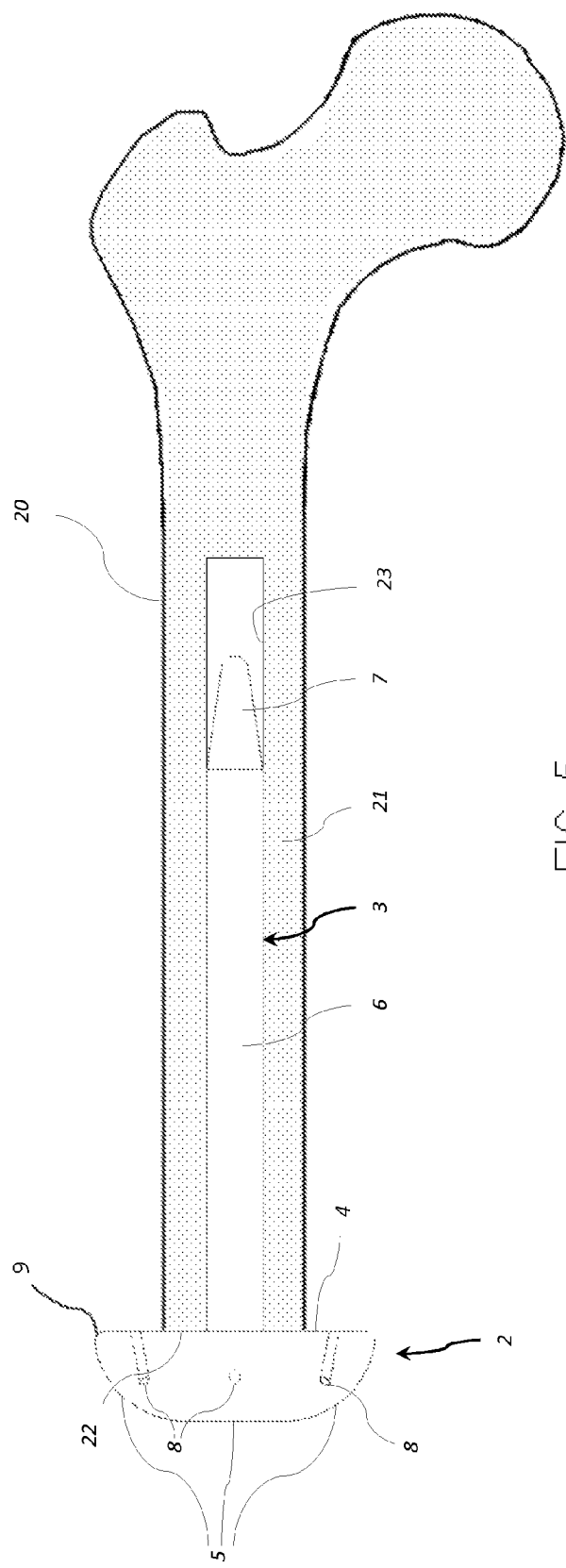
FIG. 5 is a cross-sectional view of an amputated femur with an implant according to an embodiment of this invention mounted thereto.
Figure 10:
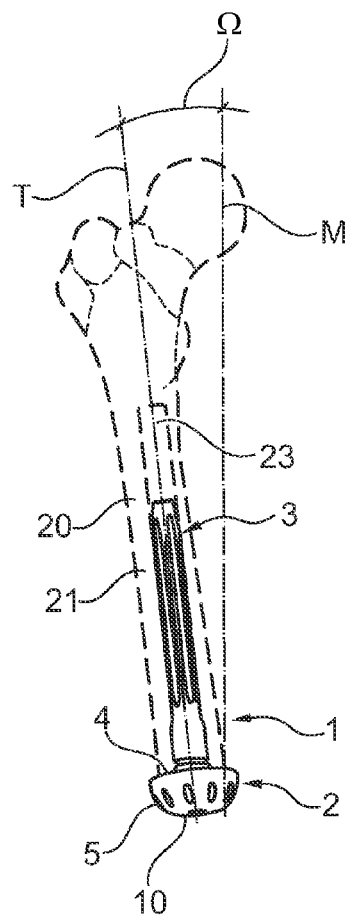
FIG. 10 is a side view of the implant of FIG. 6a, implanted in a femur of a patient.
Figure 11:
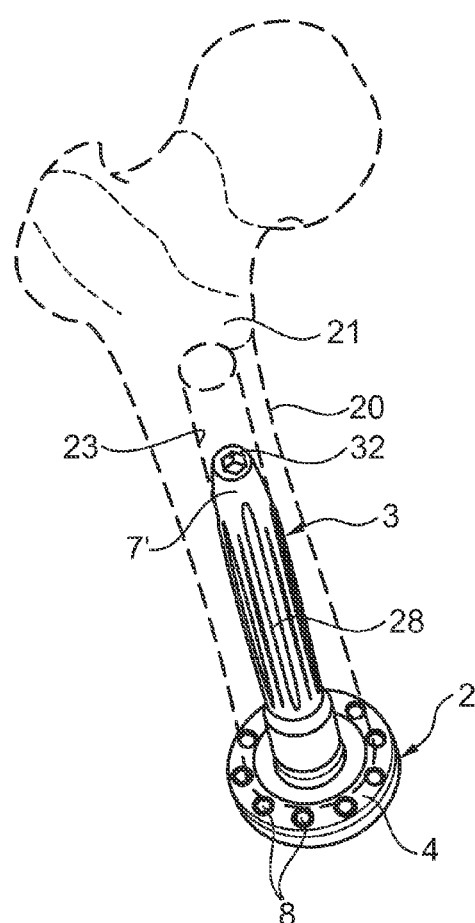
FIG. 11 is a view in perspective of the implant of FIG. 6a, implanted in a femur of a patient.

The stem 3 comprises a stem portion 6 that is preferably cylindrical and straight having a length l1 and a tapered tip 7 having a length l3. The tip 7 may end with a rounded extremity having a radius r3 as shown in FIGS. 1, 2 and 5. The tapered tip 7 and rounded extremity are configured to enable easy and smooth insertion of the stem in the medullary canal of an amputated femur bone, whereby the medullary canal 23 is reamed or drilled by the surgeon in order to ensure that the diameter and length of the surgically prepared medullary canal allows full and smooth insertion of the stem without apply excessive forces on the femur bone shaft 20. In a variant, the tapered tip 7', as shown in the embodiment of FIGS. 6 to 11, may include a tool portion 32 configured to engage a corresponding tool used to apply torque to the stem during assembly of the stem to the base. The tool portion may for instance comprise a tool socket recess 32, being formed for instance in the shape of a hexagon-socket, as best illustrated in FIG. 11. Other shapes of recesses 32 may be chosen for engagement with a corresponding tool to apply torque on the stem relative to the base.

Depending on the size and weight of the patient and the dimensions of the patient's femur as well as the site of the amputation, the length l1 and diameter d3 of the stem portion 6 may vary in the preferential range of 120 mm>l1>80 mm, and 20 mm>d3>8 mm.

The length l3 of the tapered tip 7, 7' may be preferably in the range of 15 to 25 mm, for instance at or around 20 mm. In case the stem 3 has a rounded tip as shown in FIG. 2, the tip radius r3 may be for instance around 2 mm.

The above mentioned preferred stem length l1 and diameter d3 provide great implant stability and fixing in a femoral bone and a strong material connection to the base 2 while allowing a large range of implant possibilities from just above the knee to close to the greater trochanter. The surface of the stem 3 may be smooth, or may be provided with a surface coating or surface finish that promotes osseo-integration.

In the embodiments of FIGS. 6 to 11, the stem 3 comprises a plurality of longitudinal recesses 28 and longitudinal ridges 35 distributed around the stem 3 and extending in the axial direction A corresponding to the direction of the medullary canal. The longitudinal ridges 35 improve anchoring of the stem in the medullary canal, especially in relation to preventing rotation of the implant, and may be configured to engage the surface of the medullary canal with a slight force fit. The longitudinal recesses 28 allow evacuation of material or gas in the medullary canal during insertion of the stem. Growth of bone in the recesses will significantly increase the anchoring strength of the stem to the femur. The longitudinal ridges may further be provided with longitudinal grooves 36 that are narrower than the longitudinal recesses. The grooves reduce the frictional force during insertion and improve grip of the stem in the medullary canal. The surgeon may also apply a thin coating of bone cement on the stem and/or in the machine finished medullary canal in order to solidly fix the stem to the femur bone shaft. The longitudinal recesses 28 and grooves 36 also allow bone cement and/or any other osseo-integration promoting material to be received therein.

In FIGS. 6 to 11 the recesses 28 extend almost over the entire length l1 of the stem 3, but within the scope of the invention it is possible to provide recesses 28 that extend only partially along the length of the stem portion 6.

The optimal dimensions of the implant may be determined based on radiography of the patient's limb, performed in preparation of the surgical intervention.

The base 2 comprises a bone abutting surface 4, from which the stem 3 extends, and on the other side thereof a soft tissue load bearing surface 5 facing the soft tissue of the amputated limb extremity. The soft tissue load bearing surface 5 has a generally rounded shape configured to distribute the pressure developed at the extremity of a patient's amputated limb in a corresponding socket of the patient's leg prosthesis. In a preferred embodiment the bone abutting surface 4 has a circular shape with a maximum diameter d1 that, in a preferred embodiment, may be co-axially positioned with respect to the stem 3. The diameter d1 of the base may vary as a function of the patient's anatomy, in particular the weight of the patient and/or the size of the patient's femoral bone shaft and possibly also the position of the amputation. A position of the amputation site close to the knee allows a diameter generally slightly smaller than towards the hip.

The diameter d1 of the base 2 is configured to be greater than the average diameter of the femur shaft 21 of the site of amputation in order to increase the load bearing surface area of the amputation extremity. The diameter d1 may advantageously be approximately in the range of 5 to 20 mm greater than the average diameter of the femur bone shaft 21 at the site of amputation.

The soft tissue load bearing surface 5 may comprise a central portion 10 that is flat or slightly rounded and a radially outer portion 11 that has a greater degree of curvature than the central portion 10. The radially outer portion 11 joins the bone support surface 5 through a rounded edge with a radius of preferably at least around 2 mm or more in order to avoid damage of the soft tissue positioned around the base.

A first plane defined by the bone support surface 4 and a second plane defined by the central portion 10 may be oriented parallel to one another, as best illustrated in FIGS. 1-5.

In another embodiment, a first plane defined by the bone support surface 4 and a second plane defined by the central portion 10 may be oriented at an angle β to one another, as illustrated in FIGS. 7 and 11. Load bearing surface angle β is advantageously in the range of 4° to 8°, more preferably 5° to 7°, in particular 6°. The load bearing surface angle may advantageously correspond to an angle Ω formed between a mechanical axis M and an anatomical axis T of a person's thigh, as illustrated in FIG. 10. The mechanical axis M runs through a person's hip joint and the point of contact between the prosthesis and ground. The mechanical axis M is additionally defined by a person's center of gravity, however since a person in general has two legs the mechanical axis normally runs through the hip joint and the point of contact of the foot. The anatomical axis T is defined by the longitudinal direction of the femur (transfemoral amputation) or by the longitudinal direction of the shinbone (transtibial amputation).

In embodiments where the first plane and the second plane are at a non-zero angle β, the central portion 10 is arranged asymmetrically on the bone support surface 5 and not co-axially to the stem 3 and the base 2, respectively, as best illustrated in FIGS. 7 and 8. In this embodiment the second plane defined by the central portion 10 is oriented more or less perpendicular to the mechanical axis M and further the thickness of the base 2 is not constant. The angle β thus corresponds approximately to the angle Ω. This configuration advantageously allows reducing shear forces on the stump during a transfer of load on the stump.

In the embodiment of FIGS. 6-11, the central portion 10 is arranged asymmetrically on the bone support surface 5, the radially outer portion 11 is also formed in an asymmetrical manner, as best illustrated in FIG. 7. Radius $R_1$ defines the curvature of the radially outer portion 11 on a first side of the base 2 where the outer portion 11 has a first thickness $l_1$ and Radius $R_2$ defines the curvature of the radially outer portion 11 on a second side of the base 2 where the outer portion 11 has a second thickness $l_2$. It can be seen that the first thickness $l_1$ is greater than the second thickness $l_2$ and the second plane is oriented perpendicular to the mechanical axis M. The radius $R_1$ and radius $R_2$ may be identical. In a variant, the radius $R_1$ and radius $R_2$ may however have different values. In the latter variant, the two different radii converge so that the radially outer portion 11 is continuous around the circumference of the base 2.

The radially outer portion 11 may have a spherical or essentially spherical shape. In a variant it may have an elliptical or parabolic or other slightly off-spherical shape.

The radially outer portion 11 is adapted to provide a homogeneous distribution of pressure between the load bearing surface and the surrounding soft tissue of the stump when the stump is received in a prosthetic limb socket (not shown). The thickness l2 of the base 2, as illustrated in FIG. 2, is selected to provide the optimal radii $R_1$, $R_2$ and central portion 10 diameter d2 taking into account the diameter d1 of the base. The average radius r1 of the radially outer portion may preferably be in the range of: 17 mm≥r1≥30 mm; The radii $R_1$ and $R_2$ illustrated in FIG. 7 may be in the same range.

Preferred diameters d1 of the base 2 may lie in the range of 40 to 60 mm. The general diameter d2 of the central portion 10 may be for instance in the range of 10 to 30 mm.

As illustrated in FIGS. 1-11 the bone support surface 4 is advantageously an essentially planar surface perpendicular to the stem 3 and configured to abut against the end 22 of an amputated limb. For these embodiments the orthopedic surgeon severs the bone at right angles to the axis of the medullary canal 23 which represents the anatomical axis T. Reaming of the medullary canal 23 is then performed to provide it with constant and accurate dimensions for a tight fit insertion of the stem therein. After severing of the bone, preferably after reaming of the medullary canal but alternatively before reaming, the severed bone surface is milled orthogonally to the anatomical axis T such that the severed bone surface 22 is perpendicular to the medullary canal. In an embodiment, the milling tool may comprise a centerpiece portion adapted for insertion in the medullary canal to centre the milling tool during the milling operation.

The base 2 seats against the severed bone surface 22, thus providing a very stable and strong support for the implant with the capacity to distribute the full weight of a person via the distal end of the amputated limb when placed in a socket of a limb prosthesis.

The orthogonal configuration of the stem and bone support surface is particularly advantageous in that it simplifies the surgeon's intervention and increases accuracy, reliability and safety of the operation. The embodiment of FIGS. 6 to 11 is particularly advantageous in that it provides the orthogonal arrangement while also orienting the central portion 10 of the load bearing surface 5 perpendicular to the mechanical axis M thus achieving the effect of reducing shear forces on the stump during a transfer of load on the stump.

The base 2 may further comprise suture holes 8 distributed around the base 2 and extending from the radially outer portion 11 of the load bearing surface 5, to the bone support surface 4, the suture holes providing anchor points for connecting the soft tissue around and to the base after it has been implanted. The diameter d4 of the suture holes 8 may be preferably between 1.5 and 2.5 mm, for instance around 2 mm. There may advantageously be 4 to 16 suture holes distributed regularly around the base, preferably in the range of 8 to 14 suture holes, for example 8 suture holes (45° between suture holes). The suture holes 8 may advantageously extend at an angle α with respect to the stem axis A, the axes of the suture holes converging together on a side facing away from the stem 3. This configuration advantageously directs the outlet of the holes on the bone support surface 4 side away from the bone 21 so as to facilitate the suturing operation. The suture hole angle α may advantageously lie in the range of: $10°≥α≥30°$.

The implant may advantageously be provided with a disposable removable film or cap (not shown) mounted over the load bearing surface 5 and an outer radial portion of the bone support surface not intended to rest against the bone, the film or cap configured to cover the suture holes to prevent bone cement or other materials from clogging or obstructing the suture holes. The cap or film may be removed by the surgeon after the implant has been inserted in the medullary canal.

The stem 3 may be configured to be connected to the base 2 via a mechanical fixing mechanism 29 comprising for instance a threaded bolt 25 and a complementary threaded bore 30. The threaded bore may be arranged in the stem 3 as illustrated in FIG. 6b. The bolt 25 is configured to engage the threaded bore 30 by extending through a passage 24 formed in the base 2, as best seen in FIGS. 6a, 6b and 8. The passage 24 extends from the soft tissue load bearing surface 5 through the entire base 2 whereby the bolt 25 is inserted into the passage 24 from the soft tissue load bearing surface 5 side and abuts against a shoulder 34 formed in the passage 24.

Figure 9B:
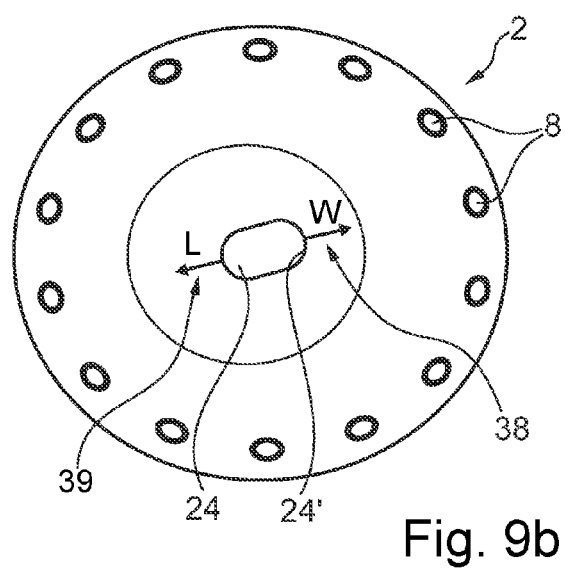
FIG. 9b is a view in the direction of arrow IXb of FIG. 7.

The passage 24 may have a non-circular portion 24' as best seen in FIG. 9b, that performs the function of a polarizing element. The polarizing element is configured to be engaged by an insertion tool (not shown) used by the surgeon to implant in the medullary canal, whereby the polarizing element allows the surgeon to rotate and position the implant in the correct orientation. Markers 38, 39 may be further provided, for instance by engraving or printing, on the base indicating the thigh inner direction (arrow "M") or thigh outer direction (arrow "L"). The polarizing element may also be performed by other cavities provided on the base, or by certain of the suture holes.

In a preferred embodiment, the base 2 further comprises a collar portion 26 extending from the bone support surface 4, through which the passage 24 extends. The collar portion 26 may advantageously have an outer conical shape 25 configured to engage a complementary conical bore surface of the stem for centering and tightly engaging the stem 3 to the base 2. The angle of the conical surfaces are configured to lock the stem to the base by frictional force when the bolt 25 engaged in the threaded bore is tightened. The fixing mechanism may have an inverse configuration whereby the cone on the base is provided in a bore and engages an outer conical surface provided on the stem, or whereby the threaded bolt extends integrally from the stem and is tightened to the base by a threaded nut. Also, the separate bolt or nut may be avoided in a variant where the threaded male and female fixing portions are directly and integrally provided on the base and stem.

The separate base 2 and stem 3 allows the implant to be adapted to the morphology of the patient, such as weight, bone structure, and position of the amputation. Stems with different diameter and/or lengths can be combined with bases of different diameter and/or shapes. This also allows the practitioner to select the stem and base if necessary during the surgical intervention to achieve the best results for load bearing capacity.

The invention claimed is:

1. Implant for transfemoral or transtibial amputation comprising a stem and a base, the base comprising a bone support surface on one side and on an opposite side a soft tissue load bearing surface, the stem extending from the base perpendicular to the bone support surface and being configured for insertion in a medullary canal of an amputated bone, the bone support surface being configured for abutment against a severed end of said amputated bone, a diameter of the base being configured to be larger than an average diameter of a shaft of said amputated bone, the soft tissue load bearing surface comprising a generally planar or slightly curved central portion and a convexly curved radially outward portion with a curvature greater than the central portion, the central portion being oriented at an angle of between 4° to 8° to the bone support surface, the base having a shape being tapered such that a diameter of the base proximate the central portion is less than a diameter of the base distal to the central portion, the base comprising a collar portion extending from the bone support surface configured to engage a complementary recess of the stem and wherein the base is formed of a single piece, wherein a radially outer portion on a lateral side of the base is curved such that the radius of curvature is greater than the radius of curvature of a radially outer portion on an opposite lateral side of the base, the two different radii converging so that the radially outer portion is continuous around a circumference of the base.

2. An implant according to claim 1, wherein the base is made of a rigid material.

3. An implant according to claim 1, wherein the central portion and the bone support surface are substantially circular or oval shaped, the centre of the circular or oval shape of the central portion being offset from the centre of the circular or oval shape of the bone support surface in a direction towards the convergence of two planes coincident with the bone support surface and the central portion respectively.

4. An implant according to claim 1, wherein the bone support surface comprises a curved rim.

5. An implant according to claim 1, wherein the central portion is oriented at an angle of between 5 to 7° to the bone support surface.

6. An implant according to claim 1, wherein the curved radially outer portion of the soft tissue load bearing surface has an average radius (r1) in the range of 17 mm to 25 mm.

7. An implant according to claim 1, wherein the soft tissue load bearing surface and the bone support surface join together via a rounded corner having a radius (r2) of at least 2 mm.

8. An implant according to claim 1, wherein the base and stem are separate parts assembled together.

9. An implant according to the claim 8, wherein the stem is fixed to the base via a mechanical fixing mechanism comprising a threaded bolt and a complementary threaded bore, the base comprising a connecting element receiving passage extending from the bone support surface through the base.

10. An implant according to claim 8, further comprising a passage through the collar portion, the collar portion having a conical surface configured to engage a conical surface of the complementary recess of the stem for centering and tightly engaging the stem to the base.

11. An implant according to claim 1, wherein the base further comprises suture holes distributed therearound and extending from the soft tissue load bearing surface to the bone support surface.

12. An implant according to claim 11, wherein the suture holes are inclined at an angle ($\alpha$) such that axes of the suture holes converge on a side opposite the stem, the angle $\alpha$ being a range of 10° to 30°.

13. An implant according to claim 11, wherein there are between 8 and 10 suture holes distributed evenly around a radially outer surface portion of the base.

14. An implant according to claim 11, wherein the suture holes extend to the radially outward portion of the bone support surface.

15. An implant according to claim 1, wherein the stem comprises a stem portion and a tapered tip, the stem portion having a length (l1) in the range of 80 mm to 120 mm.

16. An implant according to claim 1, wherein the stem comprises a plurality of longitudinal recesses and longitudinal ridges interposed between the recesses and distributed around the stem and extending in an axial direction (A) corresponding to the direction of the medullary canal.

17. An implant according to claim 1, comprising a polarizing element configured to be engaged by an insertion tool to rotate and position the implant in the correct orientation.

* * * * *